United States Patent [19]

Solyom et al.

[11] 4,342,754
[45] Aug. 3, 1982

[54] STEROID-SPIRO-OXATHIAZOLIDINE DERIVATIVES AND A PROCESS FOR THE PREPARATION THEREOF

[75] Inventors: Sandor Solyom; Katalin Szilágyi nee Farago; Lajos Toldi; Inge Schäfer; Eleonora Szondy; Janos Borvendeg; Ilona Hermann neé Szente, all of Budapest, Hungary

[73] Assignee: Richter Gedeon Vegyeszeti Gyar RT, Budapest, Hungary

[21] Appl. No.: 242,711

[22] Filed: Mar. 11, 1981

[30] Foreign Application Priority Data

Mar. 12, 1980 [HU] Hungary .................... OE 579

[51] Int. Cl.³ ............................. A61K 31/58
[52] U.S. Cl. ..................... 424/241; 260/239.5
[58] Field of Search ............... 260/239.5, 239.55; 424/241

[56] References Cited

U.S. PATENT DOCUMENTS 4,218,446  8/1980  Solyom et al. ............... 260/239.5
4,239,757 12/1980  Bodor et al. ................. 260/239.5

Primary Examiner—Elbert L. Roberts
Attorney, Agent, or Firm—Karl F. Ross

[57] ABSTRACT

New steroid-spiro-oxathiazolidine derivatives pharmaceutical compositions containing the same, and to a process for the preparation thereof are disclosed.

The new compounds have antimineral corticoide effects and have the following formula (I),

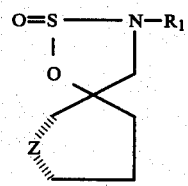

wherein
$R_1$ is a $C_{1-3}$ alkyl or a $C_{2-4}$ alkenyl group, and
Z is a group of the formulae (II) to (VI),

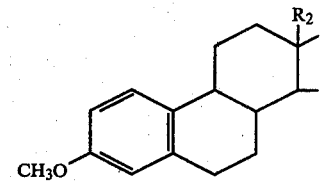

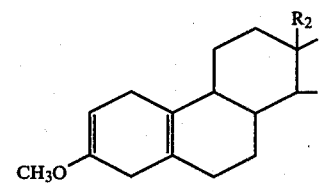

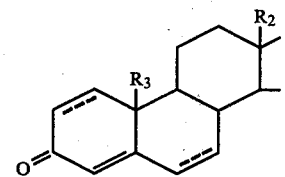

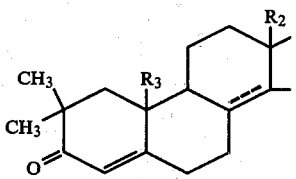

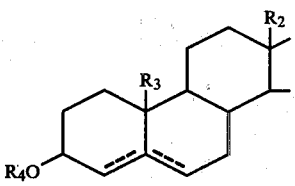

wherein
$R_2$ is methyl or ethyl,
$R_3$ is hydrogen or methyl
$R_4$ is hydrogen, a $C_{1-3}$ alkyl group, a di-($C_{1-4}$ alkyl)-amino-$C_{1-4}$ alkyl group, a $C_{2-4}$ alkylcarbonyl group, a $C_{2-4}$ alkoxycarbonyl group or a $C_{3-6}$ carboxyalkylcarbonyl group, and
the dotted lines may represent additional valence bonds, with the proviso that if Z is a group of the formula (VI), a double bond exists between the carbon atoms in positions 4 and 5 or 5 and 6, and
if $R_4$ is a di-($C_{1-4}$ alkyl)-amino-$C_{1-4}$ alkyl group or a $C_{3-6}$ carboxyalkylcarbonyl group, the compounds may also be formed as their salts.

16 Claims, No Drawings

STEROID-SPIRO-OXATHIAZOLIDINE DERIVATIVES AND A PROCESS FOR THE PREPARATION THEREOF

The invention relates to new steroid-spiro-oxathiazolidine derivatives and pharmaceutical compositions containing the same, as well as to a process for the preparation thereof.

The new compounds according to the invention correspond to the formula (I),

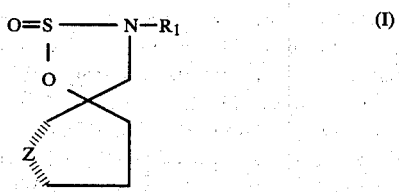

wherein
$R_1$ is a $C_{1-3}$ alkyl or a $C_{2-4}$ alkenyl group, and
Z stands for a group selected from the formulae (II) to (VI),

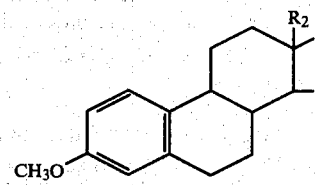

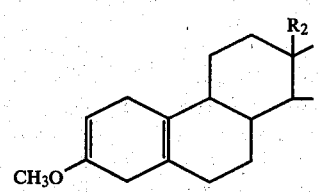

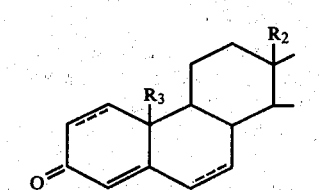

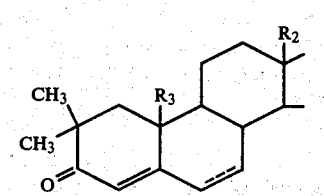

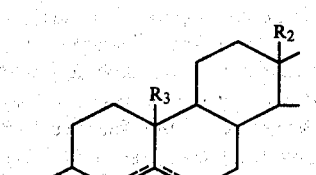

wherein
$R_2$ is methyl or ethyl,
$R_3$ is hydrogen or methyl,
$R_4$ is hydrogen, $C_{1-3}$ alkyl, di-($C_{1-4}$ alkyl)-amino-$C_{1-4}$ alkyl, $C_{2-4}$ alkylcarbonyl, $C_{2-4}$ alkoxycarbonyl or $C_{3-6}$ carboxyalkylcarbonyl, and
the dotted lines may represent additional valence bonds, with the proviso that if Z is a group of the formula (VI), a double bond exists between the carbon atoms in positions 4 and 5 or between the carbon atoms in positions 5 and 6, and
if $R_4$ is di-($C_{1-4}$ alkyl)-amino-$C_{1-4}$ alkyl or $C_{3-6}$ carboxyalkylcarbonyl, the compounds may also be formed as their salts. $R_4$ can also be H or $C_{1-3}$ alkyl.

Stereoisomers and isomeric mixtures of the compounds having the formula (I) are also embraced by the scope of the invention.

The new compounds according to the invention possess valuable antimineralocorticoid effects.

It is known that aldosterone, a hormone of the adrenal cortex, plays as important role in the salt and water transfer mechanisms of the organism. In states of pathologically increased aldosterone production this hormone inhibits the excretion of sodium ions, which involves, among others, the formation of oedemas of hepatic, renal and cardiac origin. Compounds with antimineralocorticoid effects suppress the harmful effect of this hormone, promote the excretion of sodium ions through the tubular cells of the kidney, assisting thereby the emptying of oedemas. Consequently, compounds with aldosterone-antagonistic effects exert diuretic activity, and represent a particularly valuable group of diuretics.

The new steroid derivatives of the formula (I) can be prepared according to the invention in that a compound of the formula (VII),

wherein $R_1$ and Z are as defined above, is reacted with a compound of the formula (VIII),

wherein X is halogen or 1-imidazolyl, or the two X groups form together a group of the formula (IX),

and in this latter formula $R_5$ is $C_{1-3}$ alkyl group,
and, if desired, the hydroxy group in position 3 of the resulting compound of the formula (I) is alkylated with a $C_{1-3}$ alkyl halide or a di-($C_{1-4}$ alkyl)-amino-$C_{1-4}$ alkyl halide, or is acylated with a $C_{2-4}$ alkoxycarbonyl halide, a functional derivative of a $C_{2-4}$ carboxylic acid or a functional derivative of a $C_{3-6}$ dicarboxylic acid, or is oxidized into keto group in the presence of an aluminum alcoholate,
and, if desired, the carbonyl group in position 3 of the resulting compound of the formula (I), wherein $R_1$ is as defined above and Z stands for a group of the formula (IV), and in this latter formula $R_2$ and $R_3$ are as defined above but the dotted line does not represent an additional valence bond, is reduced to hydroxy group and the resulting compound is optionally alkylated with a $C_{1-3}$ alkyl halide or a di-($C_{1-4}$ alkyl)-amino-$C_{1-4}$ alkyl halide or is optionally acylated with a functional derivative of a $C_{2-4}$ carboxylic acid or a $C_{3-6}$ dicarboxylic acid, or, if desired, a 3-keto-steroid of the formula (I) is dehydrogenated with a benzoquinone derivative to form an additional double bond between the carbon atoms in positions 1 and 2 or 6 and 7, or, if desired, a compound of the formula (I), wherein $R_1$ is as defined above and Z is a group of the formula (IV), and in this latter formula $R_2$ and $R_3$ are as defined above but the dotted line does not represent an additional valence bond, is treated with a methyl halide at low temperatures in the presence of potassium tert.-butoxide, and, if desired, a compound of the formula (I), wherein $R_1$ is as defined above and Z is a group of the formula (VI), and in this latter formula $R_4$ is di-($C_{1-4}$ alkyl)-amino-$C_{1-4}$ alkyl or $C_{3-6}$ carboxyalkylcarbonyl, is treated with an organic or mineral acid or with a base to form a salt.

According to a preferred method of the invention the starting 17α-alkylaminomethyl-17β-hydroxysteroids are reacted with thionyl chloride in the presence of an acid binding agent, preferably triethyl amine.

In another preferred method of ring formation thionyl chloride is converted first into a functional derivative, thionyl-diimidazole [see H. A. Staab, Angew. Chemie 74, 407 (1962)], and this compound is reacted without isolation, in a solution formed with an ether-type solvent, with the starting 17α-alkylaminomethyl-17β-hydroxysteroid.

If the starting substance of the formula (VII) contains a free hydroxy group in position 3, ring formation is performed preferably so that thionyl chloride is reacted first with an N-unsubstituted carbamate, preferably an urethane, in the presence of an acid binding agent, and the resulting N-sulfinyl-carbamate is reacted then, either without isolation or after isolation, with the starting 17α-alkylaminomethyl-17α-hydroxysteroid.

It has been found, unexpectedly, that when utilizing the above reagent, the starting substances with 3-alkoxy-2,5(10)-diene structure convert into spiro-oxathiazolidines with aromatic A rings. Such a conversion was not described before in the literature.

The reaction mixture obtained in the cyclization reactions described above can be processed by methods known per se, such as decomposition with water, extraction, recrystallization, column chromatography, etc.

Furthermore, according to the process of the invention the steroids which already contain the oxathiazolidine ring can be subjected to additional transformations. Thus, the hydroxy group of an oxathiazolidine-substituted steroid can be alkylated, acylated or oxidized to form a ketone, this latter ketosteroid can be dehydrogenated in order to introduce an additional double bond into the molecule, or a spiro-steroid with 3-oxo-4-ene structure can be alkylated with a methyl halide in the presence of a base, furthermore the keto group of a spiro-steroid with 3-oxo-4-ene structure can be reduced, and the resulting 3-hydroxy-4-ene-spiro-steroid can be alkylated or acylated on the hydroxy group.

All of the above reactions may also be performed prior to the formation of the spiro-ring, however, sometimes it is more preferred to subject the spiro-steroids themselves to the above transformations.

The 3-hydroxy-5-androstene-spiro-oxathiazolidines can be oxidized preferably with cyclohexanone in the presence of aluminum isopropoxide, whereupon 3-oxo-4-androstene-17-spiro-oxathiazolidine derivatives are formed. The $\Delta^1$ double bond can be introduced into the 3-oxo-4-androstene-17-spiro-oxathiazolidines preferably by dehydrogenating them with 2,3-dichloro-5,6-dicyano-1,4-benzoquinone.

Since the spiro-ring is sensitive to acids, the $\Delta^6$ double bond is introduced into the spiro-oxathiazolidines with 3-oxo-4-ene structure preferably by converting them first into an enolether derivative with ethyl orthoformate, and oxidizing the resulting enolether compound with chloranil. The 3-oxo-4-ene-spiro-oxathiazolidines can be converted into the respective 2,2-dimethyl derivatives preferably by alkylating them with methyl iodide at low temperatures (below $-50°$ C.) in the presence of potassium tert.-butoxide.

Upon formation of the oxathiazolidine ring, the steroid-17-spiro-oxathiazolidine derivatives are obtained as diastereomeric isomer pairs (exo and endo isomers), in accordance with the asymmetry possibilities of the three-ligand sulfur compounds. The isomers in which the oxygen atom adjacent to the sulfur atom is in trans position with respect to the angular alkyl group in position 18 are regarded as exo isomers.

The ratio of exo and endo isomers can be determined on the basis of the height of the doubled 18-methyl signal appearing in the $^1$H NMR spectra of isomeric mixtures. The signal with the higher chemical shift is assigned to the endo isomer.

In most of the ring-formation reactions endo and exo isomers are formed in nearly equal amounts. When thionyl-diimidazole is applied as ring closing agent, the reaction is slightly stereoselective in favor of the exo isomer. As a general rule, when purifying (e.g. recrystallizing) the someric mixture, the exo isomer tends to accumulate in the product.

Some of the starting substances applied in the process of the invention are disclosed in the Belgian patent specification No. 864,689. The preparation of the new starting substances is described in detail in the Examples.

The aldosterone-antagonizing effects of the new compounds are demonstrated by the results of the following pharmacological tests performed on rats:

(a) Tests performed according to the method of C. M. Kagawa et al. [J. Pharmacology Exp. Ther. 126, 123 (1959)]:

The rats were adenectomized 18 hours prior to the treatment. The compound under examination was administered to the animals orally in the doses indicated in Table 1. As reference substance, Spironolactone (17α-carboxyethyl-17β-hydroxy-17α-acetylthio-4-androstene-3-one lactone) was applied in an oral dose of 480 μg/animal. Simultaneously with the treatment, 12.5 μg/animal of deoxycorticosterone acetate (DOCA) were administered subcutaneously to the animals as a substance which supplements the effect of aldosterone. The sodium and potassium contents of the urine were measured, and the results were evaluated on the basis of the values.

$$\log \frac{Na^+ \cdot 10}{K^+}$$

The results of the tests performed with 3β-hydroxy-5-androstene-17S-spiro-5'-(3'-methyl-1',2',3'-oxathiazolidine)2'-oxide and 3-oxo-androsta-4,6-diene-17S-spiro-5'-(3'-methyl-1',2',3'-oxathiazolidine)-2'-oxide are summarized in Table 1.

TABLE 1

Examination of antimineralocorticoid effects on rats according to the method of Kagawa

| Compound | Dose μg/animal p.o. | N | $\log \frac{Na^+ \times 10}{K^+}$ |
|---|---|---|---|
| 3β-Hydroxy-5-androstene-17S-spiro-5'-(3'-methyl-1',2',3'-oxathiazolidine)-2'-oxide | 480 | 12 | 1.14 |
| 3-Oxo-androsta-4,6-diene-17S-spiro-5'-(3'-methyl-1',2',3'-oxathiazolidine)-2'-oxide | 480 | 8 | 1.12 |
| DOCA | — | 28 | 0.78 |
| Spironolactone | 480 | 12 | 1.14 |

N = number of animals tested

The data of Table 1 show that the compounds tested inhibit the mineralocorticoid effect of DOCA significantly, and exert an aldosterone-inhibiting effect of the same order of magnitude as the reference substance (Spironolactone).

(b) Sodium balance tests performed according to the method of Holmann [Arch. Exp. Path. u. Pharmak. 247, 419 (1964)]:

The tests were performed on selected male rats weighing 230–250 g. The rats were loaded with an intravenous infusion of isoosmotic glucose solution also containing 0.2% of sodium chloride, and the sodium excreting capacity of the kidney was monitored for 24 hours. According to the data observed, the amount of sodium ions introduced into the organism of the animals with the infusion and excreted with the urine is in equilibrium within the 4th and 13th hours.

The animals were divided into three groups. The animals in group 1 served as controls, the animals of group 2 received a mineralocorticoid agent (DOCA) only, whereas the animals of group 3 were also treated with an aldosteroneantagonizing agent.

The animals of group 2 were treated with a single subcutaneous dose of 6.25 μg/animal of DOCA simultaneously with the start of the infusion. By this single introduction of the mineralocorticoid hormone of adrenal cortex hyperaldosteronism was provoked on the animals.

The animals of group 3 were also treated with a single subcutaneous dose of 6.25 μg/animal of DOCA as described above, but also received a single subcutaneous dose of 5.5 μmg/animal of an aldosterone-antagonizing substance 2 hours after the start of the infusion. Spironolactone was used again as reference substance.

The sodium content of the urine was measured, and the extent of sodium retention was expressed in percent related to the amount of sodium ions introduced. The results are summarized in Table II.

It is apparent from the data of Table II that the sodium retention of 66.55%, provoked by DOCA, is reduced to 13.64% or 8.97%, respectively, upon administering the new compounds tested. The latter compound has a more pronounced competitive inhibiting activity.

TABLE II

Examination of antimineralocorticoid effects on rats according to the method of Holmann

| Compound | Dose per animal s.c. | N | Sodium retention, % |
|---|---|---|---|
| Control | — | 6 | 22.68 |
| DOCA | 6.25 μg | 10 | 66.55 |
| DOCA + Spironolactone | 6.25 μg 5.5 mg | 9 | 5.36 |
| DOCA + 3β-Hydroxy-5-androstene-17S-spiro-5'-(3'-methyl-1',2',3'-oxathiazolidine)-2'-oxide | 6.25 μg 5.5 mg | 10 | 8.97 |
| DOCA + 3-Oxo-androsta-4,6-diene-17S-spiro-5'-(3'-methyl-1',2',3'-oxathiazolidine)-2'-oxide | 6.25 μg 5.5 mg | 6 | 13.64 |

N = number of animals tested

Surprisingly, the new compounds according to the invention do not exert undesired endocrine side-effects. As a particular advantage, the new compounds have no detectable antiandrogenic and gestagenic effects, in contrast to Spironolactone, which latter provokes such undesired side effects to a significant degree and may lead to adverse symptoms particularly upon a prolonged treatment.

The antiandrogenic effects of the new compounds according to the invention were tested by the modified Dorfman method [R. I. Dorfman, D. F. Stevens: Endocrinology 67, 394 (1960)].

Infantile, castrated male rats, weighing 50 g, were treated for 7 days with daily subcutaneous doses of 50 μg/animal of testosterone propionate (TP). The compounds under examination were administered subcutaneously in doses of 1 mg/animal, together with TP.

On the 8th day of the test period the animals were sacrified, the ventral prostatic lobe and the seminal vesicle gland were removed, cleaned and then weighed on a torsion balance. It is known that substances with anti-androgenic effects suppress the weight increase of accessory sexual glands. The extent of inhibition can be expressed in percents, with respect to the weight increase of the glands stimulated with TP.

In the above tests Spironolactone, when introduced in a daily dose of 0.5 or 1.0 mg/animal for 7 days, inhibits the weight increase of the ventral prostatic lobe by 35% or 45%, respectively, whereas an inhibition of 38% or 54%, respectively, can be observed on the seminal vesicle gland under the same conditions. On the contrary, the new compounds listed in Table I do not show any anti-androgenic effect in daily doses of 1.0 mg/animal.

The gestagenic effects of the new compounds according to the invention were tested by the method of Clauberg [G. Clauberg: Zentralblatt Gynaekol. 54, 2757 (1930)].

Infantile female New Zealand rabbits were treated for 5 days with daily subcutaneous doses of 5 μg/animal of oestradiol, and then the animals were treated subcutaneously for 5 days with the compound under examination. Thereafter tissue samples were taken from both uterine horns at two different heights, and after a histological processing the samples were evaluated according to McPhail.

In this test Spironolactone provoked a moderate gestagenic effect (McPH index: 0.3) when administered in daily doses of 1 mg/kg, and a marked gestagenic effect (McPH index: 2.0) could be observed after a treatment with daily doses of 5 mg/kg.

On the other hand, 3β-hydroxy-5-androstene-17S-spiro-5'-(3'-methyl-1',2',3'-oxathiazolidine)-2'-oxide, a substance with the same anti-aldosterone effect as Spironolactone, proved to be inactive in the above doses (McPH index: 0).

The new compounds of the formula (I) can be used in the therapy as pharmaceutical compositions for enteral or parenteral administration. The pharmaceutical compositions may be solid (such as tablets, coated tablets, capsules, pills, etc.), semisolid (such as suppositories) or liquid preparations (such as emulsions, suspensions, injectable solutions, etc.), and can be prepared according to methods well known in the pharmaceutical industry, utilizing conventional pharmaceutically acceptable carriers (such as talc, lactose, magnesium stearate, starch, water, vegetable oils, waxes, etc.) and/or other additives, such as preserving agents, stabilizing agents, flavoring agents, surfactants, salts for adjusting the osmotic pressure, etc.

The daily dose of the compounds according to the invention may vary from 50 to 400 mg in the treatment of adults.

The invention is elucidated in detail by the aid of the following non-limiting Examples.

EXAMPLE 1

Preparation of 3-methoxy-17β-ethyl-gona-2,5(10)-diene-17S-spiro-5'-(3'-methyl-1',2',3'-oxathiazolidine)-2'-oxide 2 g of 3-methoxy-17β-ethyl-17α-methylaminomethyl-17β-hydroxy-gona-2,5(10)-diene are dissolved in 100 ml of abs. benzene, 2 ml of triethyl amine are added to the solution, and the mixture is cooled to +5° C. A mixture of 0.46 ml of thionyl chloride and 4.6 ml of benzene is added dropwise to the stirred solution at such a rate that the temperature of the reaction mixture remains between +5° and +10° C. The reaction mixture is allowed to warm to room temperature and then stirred for 5 hours. The mixture is washed repeatedly with water in order to remove the separated triethylamine hydrochloride, thereafter the benzene phase is dried over potassium carbonate, filtered and evaporated. The residue is triturated with isopropyl ether, and the resulting crystalline crude product is recrystallized from ethanol. 1.41 g of pure 3-methoxy-17β-ethyl-gona-2,5(10)-diene-17S-spiro-5'-(3'-methyl-1',2',3'-oxathiazolidine)-2'-oxide are obtained; m.p.: 145°-147° C.

EXAMPLE 2

Preparation of 3-methoxy-oestra-2,5(10)-diene-17S-spiro-5'-(3'-methyl-1',2',3'-oxathiazolidine)-2'-oxide

Method "A"

One proceeds as described in Example 1 with the difference that 2 g of 3-methoxy-17α-methylaminomethyl-17β-hydroxy-oestra-2,5(10)-diene are applied as starting substance. The crude product is recrystallized from ethyl acetate to obtain 1.25 g of 3-methoxy-oestra-2,5(10)-diene-17S-spiro-5'-(3'-methyl-1',2',3'-oxathiazolidine)-2'-oxide, a 2:1 mixture of exo and endo isomers; m.p.: 164°-167° C.

Method "B"

A solution of 1.44 ml of thionyl chloride in 15 ml of tetrahydrofuran is added dropwise, within 15 minutes, to a cold (5° C.) solution of 5.44 g of imidazole in 60 ml of tetrahydrofuran. The resulting suspension is stirred for 2 hours, then filtered, and the precipitate is washed with tetrahydrofuran. The solution is cooled to +5° C., and a solution of 2.98 g of 3-methoxy-17α-methylaminomethyl-17β-hydroxy-oestra-2,5(10)-diene in 50 ml of tetrahydrofuran is added dropwise to it within 30 minutes. The reaction mixture is stirred at room temperature for 2 hours and then evaporated. The residue is admixed with 200 ml of a 5% aqueous sodium hydrocarbonate solution, and the product is extracted with dichloromethane. The dichloromethane solution is washed with water, dried, evaporated, and the resulting crystalline crude product is washed on the filter with isopropyl ether. 2.91 g of 3-methoxy-oestra-2,5(10)-diene-17S-spiro-5'-(3'-methyl-1',2',3'-oxathiazolidine)-2'-oxide, a 4:1 mixture of exo and endo isomers, are obtained; m.p.: 152°-154° C.

1 g of the crude product is recrystallized from 10 ml of ethyl acetate to obtain 0.44 g of a substance melting at 167°-168° C., which consists of about 95% of the exo isomer.

EXAMPLE 3

Preparation of 3-oxo-oestr-4-ene-17S-spiro-5'-(3'-methyl-1',2',3'-oxathiazolidine)-2'-oxide One proceeds as described in Example 1 with the difference that 2 g of 3-oxo-17α-methylaminomethyl-17β-hydroxy-oestr-4-ene are applied as starting substance. The crude product is recrystallized from ethanol to obtain 0.66 g of crystalline 3-oxo-oestr-4-ene-17S-spiro-5'-(3'-methyl-1',2',3'-oxathiazolidine)-2'-oxide, m.p.: 195°-199° C. $\lambda_{max}$: 238 nm (E=18,100). Upon concentrating the mother liquor further 1.54 g of the product are obtained, m.p.: 130°-135° C. (this fraction is an isomeric mixture containing the endo and exo isomers in a ratio of about 10:1).

The starting substance can be prepared e.g. as follows:

8 g of 3-methoxy-17α-methylaminomethyl-17β-hydroxy-oestra-2,5(10)-diene are suspended in 140 ml of methanol, and a mixture of 10 ml of concentrated hydrochloric acid and 5 ml of water is added to it. The reaction mixture is stirred at 60° C. for 3 hours, thereafter the resulting solution is cooled and poured onto 500 ml of an ice-cold 5% aqueous potassium carbonate solution. The separated substance is extracted with dichloromethane. The dichloromethane solution is washed with water, dried over magnesium sulfate, filtered, and the filtrate is evaporated. The residue is recrystallized from ethyl acetate to obtain 5.67 g of 3-oxo-17α-methylaminomethyl-17β-hydroxy-oestr-4-ene, m.p.: 160°-165° C., $[\alpha]_D^{20}$=0° (c=0.5%. in chloroform).

EXAMPLE 4

Preparation of 3-methoxy-oestra-1,3,5(10)-triene-17S-spiro-5'-(3'-methyl-1',2',3'-oxathiazolidine)-2'-oxide

Method "A"

A solution of 0.70 g of N-sulfinyl-urethane in 7 ml of dichloromethane is added dropwise, within 30 minutes, to a stirred solution of 1.65 g of 3-methoxy-17α-methylaminomethyl-oestra-1,3,5(10)-triene-17β-ol [K. Ponsold, M. Hübner, R. Schnabel, J. Strecke: Arzneimittelforschung 24, 896 (1974)] in 20 ml of dichloromethane. Addition is performed at room temperature. After 1.5 hours of reaction the mixture is shaken with water, dried over magnesium sulfate and evaporated. The resulting crude product, weighing 2.2 g, is subjected to chromatography on a silica gel column, utilizing a 3:1 mixture of chloroform and ethyl acetate as eluting agent. The effluent is evaporated, and the resulting 1.35 g of crude product are crystallized from methanol. The crystalline 3-methoxy-oestra-1,3,5(10)-triene-17S-spiro-5'-(3'-methyl-1',2',3'-oxathiazolidine)-2'-oxide melts at 168°–171° C.

N-Sulfinyl-urethane, applied as reactant in the above process, can be prepared as follows:

A solution of 29 ml of thionyl chloride in 200 ml of dry ether is cooled to −8° C., and a solution of 35.6 g of urethane in 66 ml of pyridine and 250 ml of ether is added dropwise, within one hour, to the stirred solution. The resulting suspension is stirred for 0.5 hours under cooling and then for 2 hours at room temperature. The precipitate is filtered off and washed with ether. The clear ethereal solution is evaporated, and the residue is subjected to fractional distillation. 39.4 g of N-sulfinyl-urethane are obtained as an almost colourless liquid: b.p.: 27°–28° C./106 Pa.

Method "B"

3.31 g of 3-methoxy-17α-methylaminomethyl-17β-hydroxy-oestra-2,5(10)-diene are dissolved in 50 ml of dichloromethane, and a solution of 2.84 g of N-sulfinyl-urethane in 20 ml of dichloromethane is added dropwise to the stirred solution at room temperature within 1.5 hours. The reaction mixture is stirred for additional 4 hours, then extracted with water, dried and evaporated. Ethanol is distilled off from the residue. The oily residue crystallizes upon scraping. The crystals are filtered up, washed with isopropyl ether, and the resulting 1.72 g of crude product are subjected to chromatography on a short silica gel column, using a 3:1 mixture of chloroform and ethyl acetate as eluting agent. The product is crystallized from methanol. 1.1 g of 3-methoxy-oestra-1,3,5(10)-triene-17S-spiro-5'-(3'-methyl-1',2',3'-oxathiazolidine)-2'-oxide are obtained, m.p.: 171°–173° C. The compound is identical with the substance obtained according to Method "A". (The ratio of exo and endo isomers cannot be determined by NMR spectroscopy.)

EXAMPLE 5

Preparation of 3β-hydroxy-5-androstene-17S-spiro-5'-(3'-methyl-1',2',3'-oxthiazolidine)-2'-oxide A solution of 12.6 g of N-sulfinyl-urethane in 42 ml of dichloromethane is added dropwise, at room temperature within 15 minutes, to a stirred suspension of 14.0 g of 3β,17β-dihydroxy-17α-methylaminomethyl-5-androstene in 140 ml of dichloromethane. Thereafter the mixture is stirred for one hour at room temperature and then stirred and refluxed for a further hour. The mixture is allowed to cool, diluted with 100 ml of dichloromethane, and washed twice with 60 ml of a 10% aqueous sodium hydrocarbonate solution, each, and thrice with 60 ml of water, each. The aqueous phases, which form an emulsion, are re-extracted with dichloromethane. The organic phases are combined, dried over magnesium sulfate and evaporated. The oily residue is convered with 15 ml of isopropyl ether and scraped to effect crystallization. The resulting 14.37 g of crude product are recrystallized from 170 ml of methanol. 5.55 g of 3β-hydroxy-5-androstene-17S-spiro-5'-(3'-methyl-1',2',3'-oxathiazolidine)-2'-oxide are obtained; the product contains the exo and endo isomers in a ratio of about 2:1. This product melts first at 121°–124° C., then recrystallizes and melts again at 170°–174° C.

The mother liquor obtained in the recrystallization step is concentrated to one-fifth of its volume, and the concentrate is cooled. 7.10 g of an isomeric mixture are obtained. This product rearranges at 158° C. and then melts at 177°–179° C. The latter crystal fraction differs from the former one only in the ratio of the isomers.

EXAMPLE 6

Preparation of 3-oxo-4-androstene-17S-spiro-5'-(3'-methyl-1',2',3'-oxathiazolidine)-2'-oxide A mixture of 11.37 g of 3β-hydroxy-5-androstene-17S-spiro-5'-(3'-methyl-1',2',3'-oxathiazolidine)-2'-oxide, prepared as described in Example 5, 150 ml of toluene, 6.75 g of aluminium isopropoxide and 93 ml of cyclohexanone is stirred and refluxed for 6 hours. The reaction mixture is allowed to cool, diluted with 200 ml of benzene, 180 ml of a 1 n aqueous sodium hydroxide solution are added, and the resulting mixture is stirred for 0.5 hour. The phases are separated from each other, the emulsion phase is destructed by filtration, and the aqueous phase is re-extracted twice with 50 ml of benzene, each. The organic phases are combined, washed twice with 90 ml of 1 n aqueous sodium hydroxide solution, each, and then four times with 100 ml of 5% aqueous sodium chloride solution, each, dried, and evaporated. Ethanol is distilled off from the residue. The oily residue is covered with isopropyl ether and scraped to effect crystallization. The crystals are filtered off, and the mother liquor is treated with n-hexane to obtain a further crystal fraction. The 8.27 g of crude product are dissolved in ethanol, the solution is decolourized with carbon, filtered, and the filtrate is concentrated. 5.25 g of the recrystallized product are obtained; m.p.: 174°–176° C. Upon a repeated recrystallization from ethanol a mixture containing the exo and endo isomers in a ratio of about 5:1 is obtained, which melts at 189°–191° C.

EXAMPLE 7

Preparation of 3-oxo-androsta-1,4-diene-17S-spiro-5'-(3'-methyl-1',2',3'-oxathiazolidine)-2'-oxide A mixture of 2.26 g of 3-oxo-4-androstene-17S-spiro-5'-(3'-methyl-1',2',3'-oxathiazolidine)-2'-oxide, prepared as described in Example 6, 30 ml of benzene and 2.02 g of 2,3-dichloro-5,6-dicyano-1,4-benzoquinone (DDQ) is refluxed. After 8 hours of reaction further 30 ml of benzene and 0.70 g of DDQ are added to the mixture, and refluxing is continued for additional 16 hours. The reaction mixture is cooled, the benzene solution is removed from the separated solid by decanting, the solid is stirred thrice with 20 ml of benzene, each, the benzene phases are decanted and then combined. The resulting solution is washed twice with 30 ml of an aqueous solution containing 1% of sodium hydroxide and 0.5% of sodium dithionite, each, then with 10 ml of 1 n aqueous sodium hydroxide solution and finally with saline. The organic phase is dried, evaporated, and the oily residue is treated with isopropyl ether to effect crystallization. The crude product is recrystallized from ethyl acetate. 0.40 g of pure 3-oxo-androsta-1,4-diene-17S-spiro-5'-(3'-methyl-1',2',3'-oxothiazolidine)-2'-oxide, 1:1 mixture of exo and endo isomers, are obtained; m.p.: 189°-191° C. UV $\lambda_{max}.^{EtOH}$: 242 nm (E=14,000).

EXAMPLE 8

Preparation of 3-oxo-androsta-4,6-diene-17S-spiro-5'-(3'-methyl-1',2',3'-oxathiazolidine)-2'-oxide 6.25 g of 3-oxo-4-androstene-17S-spiro-5'-(3'-methyl-1',2',3'-oxathiazolidine)-2'-oxide, prepared as described in Example 6, are dissolved in a mixture of 28 ml of ethyl orthoformate and 62 ml of ethanol at 50° C. 0.62 g of p-toluenesulfonic acid are added to the stirred solution, and the mixture is stirred for 1.5 hours. The reaction mixture is cooled, a few drops of pyridine are added, and the mixture is poured onto 1 liter of an ice-cold 10% aqueous sodium hydrocarbonate solution under stirring. The mixture is stored in a refrigerator for some hours, the separated crystalline product is filtered off, washed with water and dried. The resulting enol ether, weighing 6.43 g, is dissolved in 180 ml of acetone containing 5% of water, and 3.95 g of chloranil are added to the stirred solution. The mixture is stirred for 6 hours in the dark, and the resulting solution is concentrated at 35°-40° C. The residue is admixed with 200 ml of a 5% aqueous sodium hydrocarbonate solution, and the mixture is extracted with ethyl acetate. The organic phase is washed with water, dried and evaporated. The dark, oily residue is subjected to chromatography on 100 g of neutral aluminium oxide, utilizing a 3:1 mixture of chloroform and ethyl acetate as eluting agent. The fractions which contain the pure product are combined and evaporated. The oily residue is dissolved in 4 ml of ethyl acetate, and 25 ml of isopropyl ether are added to the solution. 2.60 g of a yellow, crystalline product separates, which is a 3:2 mixture of the exo and endo isomers. The product melts at 110°-111° C. After recrystallization from isopropyl ether the melting point raises to 114°-116° C. UV $\lambda_{max}.^{EtOH}$: 282 nm (E=21,400).

EXAMPLE 9

Preparation of 2,2-dimethyl-3-oxo-4-androstene-17S-spiro-5'-(3'-methyl-1',2',3'-oxathiazolidine)-2'-oxide A solution of 5.0 g of 3-oxo-4-androstene-17S-spiro-5'-(3'-methyl-1',2',3'-oxathiazolidine)-2'-oxide, prepared as described in Example 6, in 40 ml of tetrahydrofuran and 20 ml of methyl iodide is cooled to −70° C., and a suspension of 10 g of potassium tert.-butoxide in 50 ml of tetrahydrofuran is added dropwise to the stirred solution within 10 minutes. After 25 minutes of reaction additional 7 g of potassium tert.-butoxide are added to the mixture in 30 ml of tetrahydrofuran. Stirring is continued for 15 minutes, and then the mixture is poured into 1200 ml of saturated aqueous ammonium chloride solution. The mixture is extracted four times with 100 ml of ethyl acetate, each, the organic solutions are combined, washed with 100 ml of a 2% aqueous sodium thiosulfate solution and then twice with 100 ml of a 5% aqueous sodium chloride solution, each, dried and evaporated. The crystalline residue is filtered off and washed with isopropyl ether. The resulting 3.25 g of crude product, melting at 172°-174° C., are recrystallized from ethanol to obtain 2.82 g of 2,2-dimethyl-3-oxo-4-androstene-17S-spiro-5'-(3'-methyl-1',2',3'-oxathiazolidine)-2'-oxide, m.p.: 178°-179° C. The product is a 2:1 mixture of the exo and endo isomers. UV $\lambda_{max}.^{EtOH}$: 239 nm (E=16,500).

EXAMPLE 10

Preparation of 3β-acetoxy-5-androstene-17S-spiro-5'-(3'-methyl-1',2',3'-oxathiazolidine)-2'-oxide 2.1 g of 3β-hydroxy-5-androstene-17S-spiro-5'-(3'-methyl-1',2',3'-oxathiazolidine)-2'-oxide, prepared as described in Example 5, are dissolved in a mixture of 20 ml of benzene, 2.6 ml of pyridine and 2.8 ml of acetic anhydride, and the solution is refluxed for 5 hours. The solution is allowed to cool, washed twice with 50 ml of saturated aqueous sodium hdyrocarbonate solution, each, and then with 5% aqueous sodium chloride solution, dried and evaporated. The crystalline residue is admixed with petroleum ether, filtered, and, if desired, the resulting 1.90 g of product (m.p.: 177°-179° C.) is recrystallized from methanol. The exo isomer accumulates in the recrystallized product; m.p.: 204°-205° C.

EXAMPLE 11

Preparation of 3β-methoxy-5-androstene-17S-spiro-5'-(3'-methyl-1',2',3'-oxathiazolidine)-2'-oxide 1.14 g of 3β-hydroxy-5-androstene-17S-spiro-5'-(3'-methyl-1',2',3'-oxathiazolidine)-2'-oxide, prepared as described in Example 5, are dissolved in 12 ml of tetrahydrofuran, and 0.27 g of a sodium hydride dispersion containing 20% of paraffine oil are added to the solution at room temperature. When the effervescence of the mixture ceases, 1.70 g of methyl iodide are added, and the mixture is warmed to 50° C. After 5 hours of reaction the mixture is poured into 120 ml of water. The separated white, crystalline substance is filtered off and washed with water until neutral.

The resulting 1.07 g of crude product, melting at 124°-128° C., are dissolved in 20 ml of methanol, the solution is decolourized with carbon, filtered, and the filtrate is concentrated to one-fifth of its original volume. 0.62 g of a white, crystalline substance separates from the concentrate, m.p.: 144°-147° C. The product is a 6:4 mixture of the exo and endo isomers.

EXAMPLE 12

Preparation of 3β-hydroxy-5-androstene-17S-spiro-5'-(3'-methyl-1',2',3'-oxathiazolidine)-2'-oxide-3-hemisuccinate 13.3 g of succinic anhydride are added to a mixture of 12.67 g of 3β-hydroxy-5-androstene-17S-spiro-5'-(3'-methyl-1',2',3'-oxathiazolidine)-2'-oxide, prepared as described in Example 5, 70 ml of toluene and 33.5 ml of pyridine. The resulting mixture is heated on a steam bath for 1.5 hours and then refluxed for 4.5 hours. Thereafter the mixture is allowed to stand at room temperature for 12 hours, whereupon the excess of succinic anhydride separates as a solid. The solid is filtered off, the mother liquor is diluted with 170 ml of benzene, washed four times with 100 ml of 2% aqueous hydrochloric acid, each, and twice with 50 ml of water, each, dried over magnesium sulfate and then evaporated. The oily residue is covered with isopropyl ether and triturated to effect crystallization. The resulting 12.48 g of crude product, melting at 168°–170° C., are dissolved in 200 ml of ethyl acetate, and the solution is concentrated to one-fifth of its original volume. 8.67 g of the pure product are obtained; m.p.: 171° C.

EXAMPLE 13

Preparation of the potassium salt of 3β-hydroxy-5-androstene-17S-spiro-5'-(3'-methyl-1',2',3'-oxathiazolidine)2'-oxide-3-hemisuccinate 8.60 g of 3β-hydroxy-5-androstene-17S-spiro-5'-(3'-methyl-1',2',3'-oxathiazolidine)-2'-oxide-3-hemisuccinate, prepared as described in Example 12, are dissolved in a mixture of 250 ml of methanol and 35.5 ml of a 2.85 w/v % aqueous potassium hydroxide solution under shaking. The solution is evaporated at 40°–45° C., the crystalline residue is dissolved in ethyl alcohol, and evaporated again. This latter operation is repeated twice more. The residue is admixed with dry ethyl acetate and filtered.

The resulting 8.81 g of crude product are dissolved in 240 ml of ethanol, the solution is decolourized with carbon, filtered, and concentrated to 50 ml. 6.14 g of 3β-hydroxy-5-androstene-17S-spiro-5'-(3'-methyl-1',2',3'-oxathiazolidine)-2'-oxide-3-hemisuccinate potassium salt separate from the concentrate; m.p.: 236°–237° C. The product is well soluble in water.

EXAMPLE 14

Preparation of 3β-hydroxy-4-androstene-17S-spiro-5'-(3'-methyl-1',2',3'-oxathiazolidine)-2'-oxide A suspension of 0.75 g of 3-oxo-4-androstene-17S-spiro-5'-(3'-methyl-1',2',3'-oxathiazolidine)-2'-oxide, prepared as described in Example 6, in 20 ml of methanol is cooled to 0° C., and 0.09 g of sodium borohydride are added to it under stirring. The solution, which forms after 0.5 hour of reaction, is maintained at a temperature of 0° C. to 5° C. for further 2 hours, and then poured onto 200 ml of water. The separated product is filtered off and washed with water until neutral. The resulting 0.78 g of crude product are dissolved in ethyl acetate, and the solution is concentrated to one-fifth of its original volume. 0.50 g of 3β-hydroxy-4-androstene-17S-spiro-5'-(3'-methyl-1', 2', 3'-oxathiazolidine)-2'-oxide separate from the concentrate. The pure product, which is a single isomer, melts at 172°–175° C. $[\alpha]_D^{20} = +77.3°$ (c=0.5%, in chloroform).

EXAMPLE 15

Separation of the exo and endo isomers of 3β-hydroxy-5-androstene-17S-spiro-5'-(3'-methyl-1',2',3'-oxathiazolidine)2'-oxide 4.6 g of 3β-acetoxy-5-androstene-17S-spiro-5'-(3'-methyl-1',2',3'-oxathiazolidine)-2'-oxide, prepared as described in Example 10, are applied onto plates coated with a silica gel adsorbent layer of 0.4 mm thickness. A 7:3 mixture of cyclohexane and ethyl acetate is applied as developing solvent. The two spots, appearing at about 0.6 and 0.5 $R_f$ respectively, are separated, and the substances are eluted from the adsorbent with ethanol. The substance isolated by evaporating the eluate of the spot with higher $R_f$ value, weighing 2.42 g, is dissolved in 170 ml of methanol, 58 mg of sodium methoxide are added, and the solution is allowed to stand for 28 hours. Thereafter the solution is evaporated, and the crystalline residue is washed with water on the filter until neutral.

The resulting 1.32 g of crude product, melting at 126°–128° C., are recrystallized from methanol. 1.10 g of 3β-hydroxy-5-androstene-17S-spiro-5'-(3'-methyl-1',2',3'-oxathiazolidine)-2'-endo-oxide are obtained; m.p.: 128°–129° C. $[\alpha]_D^{20} = -21.28°$ (c=0.5%, in chloroform).

The 2.15 g of acetoxy isomer isolated from the spot with lower $R_f$ value is hydrolyzed as described above to obtain 1.55 g of crude product, melting at 222°–225° C. The crude product is recrystallized from methanol to obtain 1.45 g of 3β-hydroxy-5-androstene-17S-spiro-5'-(3'-methyl-1',2',3'-oxathiazolidine)-2'-exo-oxide; m.p.: 224°–225° C. $[\alpha]_D^{20} = -260.7°$ (c=0.5%, in chloroform).

EXAMPLE 16

Preparation of 3β-(2-diethylamino)-ethoxy-5-androstene-17S-spiro-5'-(3'-methyl-1',2',3'-oxathiazolidine)-2'-oxide 1.50 g of sodium hydride, containing 20% of paraffine oil, are added under stirring and ice-cooling to a solution of 3.79 g of 3β-hydroxy-5-androstene-17S-spiro-5'-(3'-methyl-1',2',3'-oxathiazolidine)-2'-oxide in 30 ml of dimethyl formamide. When the effervescence of the mixture ceases, a solution of 6.8 g of 2-diethylaminoethyl chloride in 8 ml of dimethyl formamide is introduced, and the reaction mixture is stirred at room temperature for 0.5 hour and then at 70° C. for 2 hours. The mixture is allowed to stand at room temperature for 16 hours and then poured onto 600 ml of water. The separated product is filtered off and washed with water until neutral.

The resulting 4.1 g of crude product are dissolved in 100 ml of warm isopropyl ether, the solution is decolourized with carbon, filtered, and the filtrate is concentrated to a final volume of 15 ml. The separated yellow, crystalline substance is filtered off. 1.9 g of a slightly tacky product are obtained: m.p.: 105°–115° C.

EXAMPLE 17

Preparation of a pharmaceutical composition

Tablets for oral administration, containing 25 mg of active agent, can be prepared e.g. with the following composition:

| | |
|---|---|
| 3β-Acetoxy-5-androstene-17S-spiro-5'-(3'-methyl-1',2',3'-oxathiazolidine)-2'-oxide | 25 mg |
| Maize starch | 128 mg |
| Polyethylene glycol 6000 | 40 mg |
| Talc | 6 mg |
| Magnesium stearate | 1 mg |
| Average weight: | 200 mg |

The tablets are provided with a film coating or sugar coating.

What we claim is:
1. A steroid-spiro-oxathiazolidine compound of the formula (I),

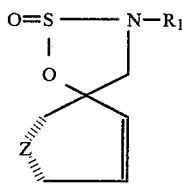

wherein
R$_1$ is C$_{1-3}$ alkyl or C$_{2-4}$ alkenyl, and
Z is one of the groups of the formulae (II) to (VI),

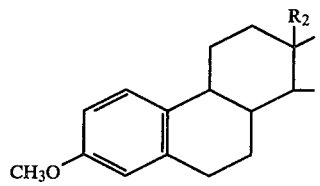

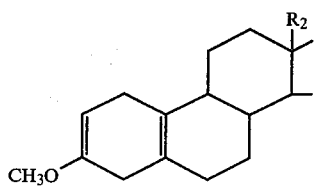

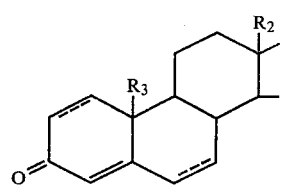

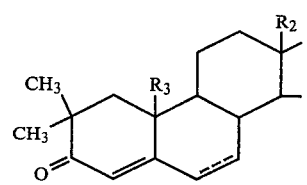

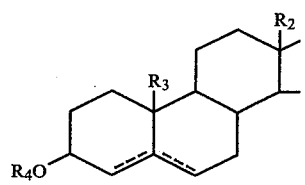

wherein
R$_2$ is methyl or ethyl,
R$_3$ is hydrogen or methyl,
R$_4$ is hydrogen, C$_{1-3}$alkyl, di-(C$_{1-4}$ alkyl)-amino-C$_{1-4}$-alkyl, C$_{2-4}$ alkoxycarbonyl or C$_{3-6}$ carboxyalkylcarbonyl, and the dotted lines can represent additional valence bonds, but if Z is a group of the formula (VI), a double bond exists either between the carbon atoms in positions 4 and 5 or between the carbon atoms in position 5 and 6 if R$_4$ is di-($_{1-4}$ alkyl)-amino-C$_{1-4}$ alkyl or C$_{3-6}$ carboxyalkylcarbonyl rather than H or C$_{1-3}$ alkyl, the compounds may also be formed as pharmaceutically effective salts by treatment with an organic or mineral acid or with a base.

2. A pharmaceutical composition containing as active ingredient an effective amount of a compound as defined in claim 1, together with a pharmaceutically acceptable carrier or diluent.

3. A process for the preparation of a compound as defined in claim 1, comprising reacting a compound of the formula (VII),

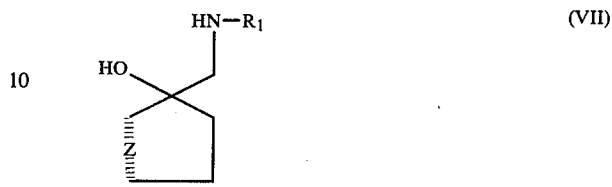

with a compound of the formula (VIII),

wherein X is halogen or 1-imidazolyl, or the two X groups form together a group of the formula (IX),

wherein R$_5$ is C$_{1-3}$ alkyl.

4. The process defined in claim 3 wherein a compound of the formula (I), wherein Z is a group of the formula (VI) and R$_4$ is di-(C$_{1-4}$ alkyl)-amino-C$_{1-4}$ alkyl or C$_{3-6}$ carboxyalkylcarbonyl, is treated with an organic or mineral acid or with a base to form a pharmaceutically effective salt.

5. A process as defined in claim 3, characterized in that the oxathiazolidine ring is formed with thionyl chloride.

6. A process as defined in claim 3, characterized in that the oxathiazolidine ring is formed with thionyl diimidazole.

7. A process as defined in claim 3, characterized in that the oxathiazolidine ring is formed with N-sulfinyl urethane.

8. A diuretic method of treatment which comprises administering to a susceptible subject an effective amount of a compound as defined in claim 1.

9. A process defined in claim 3 wherein a compound of the formula (I) wherein Z is a group of the formula (IV) and the dotted lines do not represent additional valence bonds is reduced with sodium borohydride to form a compound of the formula (I) where Z is a group of the formula (IV) wherein R$_4$ is hydrogen and wherein an additional valence bond is between the 4- and 5-positions.

10. The process defined in claim 3 wherein a compound of the formula (I) wherein Z is a group of the formula (VI) wherein R$_4$ is hydrogen is alkylated in the 3-position with a C$_1$ to C$_3$ alkyl halide to form a compound of the formula (I) wherein Z is a group of the formual (VI) wherein R$_4$ is C$_1$ to C$_3$ alkyl.

11. The process defined in claim 3 wherein a compound of the formula (I) wherein Z is a group of the formula (VI) wherein R$_4$ is hydrogen is alkylated in the 3-position with a di-(C$_1$ to C$_4$-alkyl)-amino-C$_1$ to C$_4$ alkyl halide to form a compound of the formula (I) where Z is a group of the formula (VI) wherein R$_4$ is di-(C$_1$ to C$_4$ alkyl)-amino-C$_1$ to C$_4$ alkyl.

12. The process defined in claim 3 wherein a compound of the formula (I) wherein Z is a group of the formula (VI) wherein $R_4$ is hydrogen is acylated in the 3-position to form a compound of the formula (VI) wherein $R_4$ is selected from the group which consists of $C_2$ to $C_4$ alkylcarbonyl, $C_2$ to $C_4$ alkoxycarbonyl and $C_3$ to $C_6$-carboxy-alkyl-carbonyl.

13. The process defined in claim 3 wherein a compound of the formula (I) wherein Z is a group of the formula (VI) wherein $R_4$ is hydrogen and where there is an additional valence bond between positions 5 and 6, is oxidized in the 3-position with an aluminum alcoholate to form a compound of the formula (I) and where the dotted lines do not represent additional valence bonds.

14. The process defined in claim 3 in which a compound of the formula (I) wherein Z is a group of the formula (IV) and wherein the dotted lines do not represent additional valence bonds is dehydrogenated with a benzoquinone to form a compound of the formula (I) wherein Z is a group of the formula (IV) wherein the dotted line between positions 1 and 2 represent an additional valence bond and wherein the dotted line between positions 6 and 7 does not represent an additional valence bond.

15. The process defined in claim 3 wherein a compond of the formula (I) wherein Z is a group of the formula (IV) and where the dotted lines do not represent additional valence bonds is dehydrogenated by treatment first with ethyl orthoformate and then with chloranil to form a compound of the formula (I) wherein Z is a group of the formula (IV) where the dotted line between positions 1 and 2 does not represent an additional valence bond and wherein the dotted line between positions 6 and 7 represents an additional valence bond.

16. The process defined in claim 3 wherein a compound of the formula (I) wherein Z is a group of the formula (IV) and the dotted lines do not represent additional valence bonds is treated with a methyl halide at low temperature in the presence of potassium tert.-butoxide, to yield a compound of the formula (I) where Z is a group of the formula (V) and where the dotted line does not represent an additional valence bond.

* * * * *